United States Patent [19]

Dwyer

[11] Patent Number: 5,254,767
[45] Date of Patent: Oct. 19, 1993

[54] HIGHLY SILICEOUS POROUS CRYSTALLINE MATERIAL AND ITS USE IN CONVERSION OF OXYGENATES

[75] Inventor: Francis G. Dwyer, West Chester, Pa.

[73] Assignee: Mobil Oil Corp., Fairfax, Va.

[21] Appl. No.: 623,585

[22] Filed: Jun. 22, 1984

Related U.S. Application Data

[62] Division of Ser. No. 587,327, Mar. 7, 1984, abandoned, which is a division of Ser. No. 373,451, Apr. 30, 1982, abandoned.

[51] Int. Cl.$^5$ .............................................. C07C 1/20
[52] U.S. Cl. ...................... 585/469; 585/408; 585/640; 585/739
[58] Field of Search ............... 585/408, 469, 640, 739; 502/71

[56] References Cited

U.S. PATENT DOCUMENTS

| | | | |
|---|---|---|---|
| 4,481,177 | 11/1984 | Valyocsik | 423/329 |
| 4,556,477 | 12/1985 | Dwyer | 208/111 |
| 4,574,043 | 3/1986 | Chester et al. | 208/111 |
| 4,605,488 | 8/1986 | Chester et al. | 208/111 |
| 4,717,465 | 1/1988 | Chen et al. | 208/59 |
| 4,783,555 | 11/1988 | Atkins | 502/77 |
| 4,810,357 | 3/1989 | Chester et al. | 208/97 |
| 4,814,543 | 3/1989 | Chen et al. | 585/739 |
| 4,902,406 | 2/1990 | Valyocsik | 208/118 |
| 4,919,788 | 4/1990 | Chen et al. | 208/49 |
| 5,063,038 | 11/1991 | Kirker et al. | 502/77 |
| 5,135,638 | 8/1992 | Miller | 585/739 |
| 5,137,194 | 10/1992 | Rahnim et al. | 585/671 |

*Primary Examiner*—Asok Pal
*Attorney, Agent, or Firm*—Alexander J. McKillop; Dennis P. Santini; Edward F. Kenehan, Jr.

[57] ABSTRACT

A new zeolite, designated ZSM-22, is disclosed and claimed. The new zeolite has the composition, in the anhydrous state, expressed in terms of mole ratios of oxides as follows:

$$(x)Q_2O:(y)M_{2/n}O:(z)L_2O_3:100SiO_2$$

wherein $Q_2O$ is the oxide form of an organic compound containing an element of Group 5-B (as defined in the Table of the Elements—National Bureau of Standards, Fischer Scientific Co. Catalog No. 5-702-10), e.g., N or P, preferably N, containing at least one alkyl or aryl group having at least 2 carbon atoms, M is an alkali or alkaline earth metal having a valence n, e.g., Na, K, Cs or Li and wherein $x=0.01-2.0$, $y=0-2.0$, $z=0-5$, and $L=Al$. The zeolite is useful in the process of catalytic conversion of alcohols and/or oxygenates to gasoline-grade hydrocarbons.

3 Claims, No Drawings

HIGHLY SILICEOUS POROUS CRYSTALLINE MATERIAL AND ITS USE IN CONVERSION OF OXYGENATES

This application is a division of copending U.S. application Ser. No. 587,327, filed Mar. 7, 1984, now abandoned, which is a division of U.S. application Ser. No. 373,451, filed Apr. 30, 1982, now abandoned.

BACKGROUND OF THE INVENTION

1. Field of the Invention

This invention relates to a novel siliceous porous crystalline material.

2. Description of Related Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. The cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as having a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed by the relationship of aluminum to the cations, wherein the ratio of aluminum to the number of various cations, such as Ca/2, Sr/2, Na, K, Cs or Li, is equal to unity. One type of cation may be exchanged either entirely or partially with another type of cation utilizing ion exchange. techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. The aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-35 (U.S. Pat. No. 4,016,245), zeolites ZSM-21 and ZSM-38 (U.S. Pat. No. 4,046,859), and zeolite ZSM-23 (U.S. Pat. No. 4,076,842).

The $SiO_2/Al_2O_3$ ratio of a give zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5, up to infinity. U.S. Pat. No. 3,941,871, now Re. 29,948 the entire contents of which are incorporated hereby reference, discloses a porous crystalline silicate zeolite made from a reaction mixture containing no deliberately added alumina in the recipe and exhibiting the X-ray diffraction pattern characteristic of ZSM-5 type zeolites. U.S. Pat. Nos. 4,061,724, 4,073,865 and 4,104,294, the entire contents of all three patents being incorporated herein by reference, describe crystalline silica compositions of varying alumina and metal content.

SUMMARY OF THE INVENTION

The present invention is directed to a novel highly siliceous porous crystalline material. The crystalline material of this invention has been designated as the zeolite ZSM-22 and it has a characteristic X-ray diffraction pattern, as set forth in Table 1, discussed below.

The highly siliceous material of this invention comprises crystalline, three-dimensional continuous framework silicon-containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations. Similar structures form building blocks of materials such as quartz, cristobalite and a long list of zeolite structures such as ZSM-5, ZSM-11, ZSM-12, ZSM-23, ZSM-35, ZSM-38, ZSM-48 (described in a copending U.S. application Ser. No. 56,754, filed Jul. 12, 1979), mordenite and perhaps even faujasite. Not all zeolite structures are known to exist at this time in predominantly $SiO_2$-containing compositions—so the above class of materials does not presently include zeolites such as zeolite A.

The zeolite of the present invention also contains a relatively minor amount ob $Al_2O_3$ and can produce a product with a $SiO_2$ to $Al_2O_3$ mole ratio of about 20 to about $\infty$. In the as-synthesized form, the ZSM-22 has a calculated composition, in terms of moles of oxides, after dehydration, per 100 moles of silica, as follows:

$$(x)Q_2O:(y)M_{2/n}O:(z)L_2O_3:100SiO_2$$

wherein $Q_2O$ is the oxide form of an organic compound containing an element of group 5-B (as defined in the Table of the Elements—National bureau of Standards, Fischer Scientific Co. Catalog No. 5-702-10), e.g., N or P, preferably N, containing at least one alkyl or aryl group having at least 2carbon atoms, M is an alkali metal or an alkaline earth metal having a valence n, and wherein x=0.01–2.0, y=0–2.0, z=0–5, L=Al.

ZSM-22 can further be identified by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any that are desired so long as they can pass through the channels within the zeolite crystals. Desired replacing ions are those of hydrogen, rare earth metals, metals of Groups IB, IIA, IIB, IIIA, IIIB, IVA, IVB, VIB and VIII of the Periodic Table. Among the metals, those particularly preferred are rare earth metals, manganese, zinc and those of Group VIII of the Periodic table.

ZSM-22 zeolite described and claimed herein has a definite X-ray diffraction pattern, set forth below in Table, I, which distinguishes it from other crystalline materials.

TABLE I

Most Significant Lines of ZSM-22

| Interplanar d-spacings (Å) | Relative Intensity (I/Io) |
|---|---|
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Å, corresponding to the recorded lines, were determined. In Table I, the relative intensities are given in terms of the symbols vs=very strong, s=strong, m=medium, w=weak, etc. It should be understood that this X-ray diffraction pattern is characteristic of all the species of ZSM-22 zeolite compositions. Ion exchange of the alkali metal cations with other ions results in a zeolite which reveals substantially the same X-ray diffraction pattern with some minor shifts in interplanar spacing and variation in relative intensity. Other minor variations can occur, depending on the silica to alumina ratio of the particular sample, as well as its degree of thermal treatment.

The zeolite of this invention freely sorbs normal hexane and has a pore dimension greater than about 4 Angstroms. In addition, the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10 -membered rings are preferred, although, in some instances, excessive puckering or pore blockage may render these zeolites ineffective. Twelve-membered rings do not generally appear to off sufficient constraint to produce the advantageous hydrocarbon conversions, although puckered structures exist such as TMA offretite which is a known effective zeolite. Also, such twelve-membered structures can be conceived that may be operative due to pore blockage or other causes.

Rather than attempt to judge form crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. (288° C.) and 950° F. (510° C.) to give an overall conversion between 10% and 60%. The mixture of hydrocarbons is passed at a 1 liquid hourly space velocity (LHSV), i.e., 1 volume of liquid hydrocarbon per volume of zeolite per hour over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites of the present invention are those having a constraint index in the approximate range of 1 to 12, preferably 1 to 5, and most preferably about 2.5 to about 3.0. Constraint Index (CI) values for some typical zeolites are:

| Zeolite | C.I. |
|---|---|
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that these are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite, may affect the constraint index. It will accordingly be understood by those skilled in the art that the constraint index, as utilized herein, while affording a highly useful means for characterizing the zeolites of interest is approximate, taking into consideration the manner of its determination; with probability, in some instance, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In t hose instances, a temperature of up to about 1000° F. and a liquid hourly space velocity of less than one, such as 0.1 or less, can be employed in order to achieve a minimum total conversion of about 10%.

The new ZSM-22 highly siliceous zeolite can be suitably prepared from a reaction mixture containing a source of silica, $Q_2O$, an alkali metal oxide, e.g., sodium, potassium or cesium, water, and alumina, and having a composition, in terms of mole ratios of oxides, falling within the following ratios:

| Reactants | Broad | Preferred |
|---|---|---|
| $SiO_2/Al_2O_3 =$ | 20 to $\infty$ | 30 to 1000 |
| $M_{2O/n}(Q_2O + M_{2O/n}) =$ | 0 to 0.95 | 0.1 to 0.8 | where $Q_2O$ is the oxide form of an organic compound of an element of Group 5-B of the Periodic Table, e.g., N, P. preferably N, containing at least one alkyl or aryl group having at least 2 carbon atoms, and M is an alkali or alkaline earth metal of valence n, and maintaining the mixture at crystallization temperature until crystals of the new ZSM-22 zeolite are formed. Thereafter, the crystals are separated from the liquid by any conventional means, washed and recovered. The zeolite of this invention can be used in aromatics alkylation reactions (e.g., toluene alkylation by methanol and ethylent), toluene disproportionation, selective cracking of a meta/para-cymene mixture and in conversion of various oxygenates to gasoline-grade hydrocarbons and/or chemicals, e.g., olefins.

DESCRIPTION OF PREFERRED EMBODIMENTS

Crystallization can be carried out at either static or stirred conditions in a reactor vessel, e.g., a polypropylene jar or teflon lined or stainless steel autoclaves at 80° C. (176° F.) to about 21° C. (410° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silicic acid, sodium, potassium or cesium hydroxide, and an organic compound. The organic compound contains an element of Group 5-B, such as nitrogen or phosphorus, preferably nitrogen. The preferred compounds are generally expressed by the following formula:

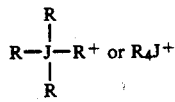

wherein J is an element of Group 5-B of the Periodic Table, e.g. N or P, preferably N, and each R is an alkyl or aryl group having at least two (2) carbon atoms or hydrogen. Suitable organic compounds are dialkylammonium compounds wherein each of the alkyl groups is the same or different and each alkyl group has two (2) to eight (8) carbon atoms, e.g., ethyl, propyl, butyl, pentyl, hexyl, heptyl or octyl. The reaction mixture can be prepared either batchwise or continuously. Crystal size an dcrystallization time of the new crystalline material will vary with the nature of the reaction mixture employed and the crystallization conditions.

The organic compounds need not be used as such. They may be produced in situ by the addition of the appropriate precursors. The precursors comprise either compounds characterized by the formula RR'R"J where R, R', and R" are selected from alkyl, substituted alkyl, aryl, substituted aryl, cycloalkyl, substituted cycloalkyl and hydrogen, and J is an element of Group 5-B, e.g. N or P, or compounds of the formula R'''X where R''' is alkyl, substituted alkyl, cycloalkyl, substituted cycloalkyl, aryl and substituted aryl and X is an electronegative group.

As set forth above, the ZSM-22 zeolite of this invention can be prepared at a relatively wide range of $SiO_2AL_2O_3$ ratios of about 20 to about $\infty$.

While synthetic ZSM-22 zeolites may be used in a wide variety of hydrocarbon conversion reaction, they are notably useful in the processes of polymerization, aromatization and cracking. Other hydrocarbon conversion processes for which ZSM-22 may be utilized in one or more of its active forms include, for example, hydrocracking and converting light aliphatics to aromatics, e.g., as disclosed in U.S. Pat. No. 3,760,024, the entire contents of which are incorporated herein by reference. Preliminary results indicate that ZSM-22 is para-selective in its catalytic reactions.

Employing a catalytically active form of the ZSM-22 catalyst for polymerization of olefins containing liquid or gaseous charge stocks, such charge stocks can be polymerized at temperatures between 290° and 450° C. (about 550° and 850° F.) at an hourly space velocity of between 0.5 and 50 WHSV (weight hourly space velocity) and a pressure of between 0.1 and 800 psig. In employing the catalyst of the present invention for aromatization gaseous or liquid charge stocks which may be olefinic or paraffinic, with or without aromatics present, such stocks can be aromatized at temperatures of between 430° and 650° C. (about 800° and 1200° F.), pressures of 1 to 10 atmospheres and space velocities of between 0.1 and 10 weight hourly space velocity (WHSV).

The ZSM-22 zeolites are also useful in the conversion of oxygenates (e.g., methanol) to gasoline-grade hydrocarbons or to chemicals, e.g., olefins. The conversion process can be conducted in a fixed bed, in a fixed bed tubular reactor or in a fluidized bed reactor. The prior art processes for carrying out such conversion with ZSM-5 and other zeolites are disclosed, e.g., in U.S. Pat. Nos. 3,894,106, 3,894,107, 3,904,508, 3,907,915, 3,931,349, 3,965,205 and 3,998,898, the entire contents of all of which are incorporated herein by reference. The ZSM-22 zeolite can be substituted for other ZSM-5 type zeolites used in the prior art. Accordingly, the process operating conditions and details will e identical to those of the aforementioned patents, except that the ZSM-22 zeolite is substituted in the process for the zeolites of the prior art. In the fluidized bed reactor, the reaction is carried out at a temperature of at least 500° F., at pressure of 1 to 200 atmospheres and at 0.5 to 50 liquid hourly space velocity (LHSV).

In a fixed bed reactor, the process is conducted in two stages. The first stage comprises conversion of the oxygenates to dimethyl ether (in a DME reactor), and the second stage conversion of the first reactor effluent to the hydrocarbon products of the reaction. Both stages of the reaction are carried out in the presence of a catalyst: the first stage with a gamma-alumina catalyst (see, e.g., U.S. Pat. No. 3,931,349), and the second stage with a ZSM-5 type zeolite catalyst, or more specifically with a ZSM-22 zeolite catalyst.

The ZSM-22 zeolite can also be used in catalytic dewaxing of petroleum stocks. Prior art processes for catalytic dewaxing of such stocks over ZSM-5 and similar zeolites are disclosed, e.g., in U.S. Pat. Nos. 3,894,938, 4,222,855, 4,137,148, 3,668,113, 3,755,138 and 4,080,397, the entire contents of all of which are incorporated herein by reference. The ZSM-22 zeolite of this invention can be substituted as the catalyst in the processes of the aforementioned patents. Accordingly, the process conditions and operating details will be the same as those in the patents, except that the new ZSM-22 zeolite is substituted in the process for the catalysts of the prior art. Thus, the dewaxing is usually carried out by passing the feedstock over the ZSM-22 catalyst, in the presence or absence of added hydrogen, and the effluent of that step may optionally be subjected to other conventional refining steps, e.g., desulfurization and/or denitrogenation. The ZSM-22 zeolite used in the dewaxing process may have incorporated therein a hydrogen transfer functional component, such as nickel, palladium or platinum, in the amount of 0.05 to 5% by weight, based on the total weight of catalyst.

In gas oil dewaxing, the catalytic dewaxing step is conducted at a temperature of about 300°–1000° F., a pressure of 0–2000 psig, and at liquid hourly space velocity (LHSV) of 0.1 to 10 with a hydrogen to hydrocarbon ratio of about 0 to about 25:1.

In lube stock dewaxing, conditions for the catalytic hydrodewaxing step include a temperature of between about 500° F. and about 675° F., a pressure of between about 100 and about 3000 psig, preferably between about 200 and about 1000 psig. The liquid hourly space velocity is between about 0.1 and about 10, preferably between about 0.5 and about 4.0, and the hydrogen to feed ratio is about 400 to about 8000, preferably about 800 to 4000 standard cubic feed (scf) of hydrogen per barrel of feed.

Synthetic ZSM-22 zeolites can be used either in the organic nitrogen-containing and alkali metal-containing form, the alkali metal form and hydrogen form or another univalent or multivalent cationic form. The as-synthesized zeolite may be conveniently converted into the hydrogen, the univalent or multivalent cationic forms by base exchanging the zeolite to remove the sodium cations by such ions as hydrogen (from acids), ammonium, alkylammonium and arylammonium including $RNH_3$, $R_3NH^+$, $R_2NH_2^+$ and $R_4N^+$ where R is alkyl or aryl, provided that steric hindrance does not prevent the cations from entering the cage and cavity structure of the ZSM-22 type crystalline zeolite. The hydrogen form of the zeolite, useful in such hydrocarbon conversion processes as isomerization of poly-substituted alkyl aromatics and disproportionation of alkyl aromatics, is prepared, for example, by base exchanging the sodium form with, e.g., ammonium chloride or hydroxide whereby the ammonium ion is substituted for the sodium ion. The composition is then calcined at a temperature of, e.g., 1000° F. (about 540° C.) causing evolution of ammonia and retention of the hydrogen proton in the composition. Other replacing cations include cations of the metals of the Periodic Table, particularly metals other than sodium, most preferably metals of Group IIA, e.g., zinc, and Groups IIIA, IVA, IB, IIB, IIIB, IVB, VIB and Group VIII of the Periodic Table, and rare earth metals and manganese.

Ion exchange of the zeolite can be accomplished conventionally, e.g., by admixing the zeolite with a solution of a cation to be introduced into the zeolite. Ion exchange with various metallic and non-metallic cations can be carried out according to the procedures described in U.S. Pat. Nos. 3,140,251, 3,140,252 and 3,140,253, the entire contents of which are incorporated herein by reference.

The ZSM-22 crystal can also be used as a catalyst in intimate combination with a hydrogenating component such as tungsten, vanadium, molybdenum, rhenium, nickel, cobalt, chromium, manganese, or a noble metal such as platinum or palladium where a hydrogentaion-dehydrogenation function is desired. Such component can be exchanged into the composition, impregnated therein or physically intimately admixed therewith. Such component can be impregnated in or onto the zeolite, for example, in the case of platinum, by treating the zeolite with a solution containing a platinum metal-containing ion. Thus, suitable platinum compounds include chloro-platinic acid, platinous chloride and various compounds containing the platinum tetramine-platinum complex. Combinations of the aforementioned metals and methods for their introduction can also be used.

Synthetic ZSM-22 zeolite, when employed either as an absorbent or as a catalyst in a hydrocarbon conversion process, should be at least partially dehydrated. This can be accomplished by heating the zeolite to a temperature in the range of about 200° C. to about 600° C. in an inert atmosphere, such as air nitrogen for about 1 to about 48 hours. Simple dehydration of the crystal can also be performed at lower temperatures, such as room temperature, merely by placing the ZSM-22 zeolite type crystal in a vacuum, but a longer time is required to obtain a sufficient degree of dehydration.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials, such as clays, silica and/or metal oxides. The clays, silica and/or metal oxides may be either naturally occurring or in the form of gelatinous precipitates or gels including mixtures of silica and metal oxides. The use of such additional active material in conjunction with the new ZSM-22 crystal, i.e., combined therewith, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions, Such materials, e.g., clays or oxides, function as binders for the catalyst. It is desirable to provide a catalyst having good crush strength because in commercial use it is desirable to prevent the catalyst from breaking down into powder-like materials. These clay binders are normally employed for the purpose of improving the crush strength of the catalyst.

Naturally occurring clays which can be composited with the new zeolite include the montmorillonite and kaolin family, which families include the subbentonites, and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the ZSM-22 zeolite can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The relative proportions of finely divided crystalline material and inorganic oxide gel matrix vary widely, with the crystal content ranging from about 1 to about 90% by weight.

In order to more fully illustrate the nature of the invention and the manner of practicing same, the following examples are presented.

In the example which follow, and elsewhere in the specification, whenever adsorption data are set forth for comparison of sorptive capacities for water, cyclohexane and n-hexane, they were determined as follows:

A weighed sample of the calcined zeolite was contacted with the desired pure adsorbate vapor in an adsorption chamber, evacuated to <1 mm pressure and contacted with 12 mm Hg of water vapor or 20 mm Hg of n-hexane or cyclohexane vapor, pressures less than the vapor-liquid equilibrium pressure of the respective adsorbate at room temperature. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the pressures to the aforementioned control levels. Sorption was complete when the pressure change was not sufficient to activate the manostat. The increase in weight was calculated as the adsorption capacity of the sample in g/100 g of calcined absorbent.

EXAMPLE 1

ZSM-22 was crystallized by reacting a silicate solution with an acid alum solution, both prepared as set forth below.

The silicate solution was prepared by adding, to 281 grams (g) of distilled water, 10.2 g of the 98.1% by weight sodium hydroxide (NaOH) solution, and 225 g of Q-brand sodium silicate (a brand name of sodium silicate comprising, in percent by weight, 28.5% $SiO_2$, 8.8% $Na_2O$, and 62.7% water).

The acid alum solution was prepared by adding to 385 g of distilled water, 18.5 g of sulfuric acid (96.4% by weight), 46.4 g of diethylamine hydrochloride and 7.7 g of aluminum sulfate [$Al_2(SO_4)_3 \times 14H_2O$].

The silicate solution and the acid aluminate solution were mixed separately in a Waring blender and then transferred to a Teflon-lined reactor bomb. The bomb was placed in a silicone oil bath at 300° F. (149° C.) for 3 days. After 3 days the bomb was removed from the bath and the contents transferred to a plastic jar and held for 11 days at room temperature. At the end of 11 days the reaction mixture was returned to the bomb and crystallization resumed at 300° F. After a total of 16 days at 300° F. the bomb was sampled, the sample was filtered out of solution, water washed and dried. The crystalline product was identified from its X-ray diffraction pattern, set forth below, as the new zeolite ZSM-22. Chemical analysis of the product gave the following results:

| | |
|---|---|
| $SiO_2$ | 97.0% wt |
| $Al_2O_3$ | 1.93% wt |
| Na | 0.30% wt |
| N | 0.76% wt |

Adsorption capacities of the washed, dried and calcined product were:

| | |
|---|---|
| water | 5.0% wt |
| cyclohexane | 0.6% wt |
| h-hexane | 3.7% wt |

X-ray analysis of the product, as synthesized, revealed that the crystals have the following X-ray diffraction pattern:

| Line | 2Theta | D(Å) | I/IMAX |
|---|---|---|---|
| 1 | 7.93 | 11.15 | 51* |
| 2 | 8.10 | 10.91 | 65 |
| 3 | 8.79 | 10.06 | 20* |
| 4 | 8.94 | 9.89 | 7* |
| 5 | 10.11 | 8.75 | 14 |
| 6 | 11.90 | 7.44 | 1* |
| 7 | 12.75 | 6.94 | 23 |
| 8 | 13.14 | 6.74 | 3* |
| 9 | 13.88 | 6.38 | 4* |
| 10 | 14.76 | 6.00 | 5* |
| 11 | 15.48 | 5.72 | 3* |
| 12 | 15.86 | 5.59 | 4* |
| 13 | 16.33 | 5.43 | 10 |
| 14 | 16.52 | 5.37 | 5* |
| 15 | 17.18 | 5.16 | 1* |
| 16 | 17.73 | 5.00 | 1* |
| 17 | 19.38 | 4.58 | 12* |
| 18 | 20.32 | 4.37 | 100 |
| 19 | 20.78 | 4.27 | 10* |
| 20 | 21.56 | 4.12 | 12 |
| 21 | 22.11 | 4.02 | 7* |
| 22 | 23.07 | 3.86 | 36* |
| 23 | 23.17 | 3.84 | 32* |
| 24 | 23.73 | 3.75 | 19* |
| 25 | 24.07 | 3.70 | 36* |
| 26 | 24.20 | 3.68 | 82 |
| 27 | 24.59 | 3.62 | 59 |
| 28 | 25.69 | 3.47 | 42 |
| 29 | 26.65 | 3.35 | 10 |
| 30 | 26.99 | 3.30 | 8 |
| 31 | 27.67 | 3.22 | 2 |
| 32 | 28.50 | 3.13 | 1 |
| 33 | 29.23 | 3.06 | 3 |
| 34 | 29.98 | 2.981 | 6 |
| 35 | 30.37 | 2.943 | 4 |
| 36 | 30.78 | 2.905 | 2 |
| 37 | 32.14 | 2.785 | 2 |
| 38 | 32.72 | 2.737 | 3 |
| 39 | 33.00 | 2.714 | 2 |
| 40 | 34.20 | 2.622 | 1* |
| 41 | 35.62 | 2.520 | 20 |
| 42 | 36.00 | 2.495 | 2* |
| 43 | 36.60 | 2.455 | 2 |
| 44 | 36.90 | 2.436 | 8 |
| 45 | 37.39 | 2.405 | 3 |
| 46 | 38.03 | 2.366 | 6 |
| 47 | 40.25 | 2.241 | 1 |
| 48 | 43.77 | 2.068 | 4 |
| 49 | 44.45 | 2.038 | 3 |

| Line | 2Theta | D(Å) | I/IMAX |
|------|--------|------|--------|
| 50 | 45.03 | 2.013 | 4 |
| 51 | 45.37 | 1.999 | 5 |
| 52 | 46.38 | 1.958 | 1 |
| 53 | 47.30 | 1.922 | 1 |
| 54 | 47.76 | 1.904 | 3 |
| 55 | 48.57 | 1.874 | 8 |
| 56 | 49.30 | 1.848 | 1 |
| 57 | 49.78 | 1.832 | 1 |
| 58 | 51.13 | 1.786 | 3 |
| 59 | 52.01 | 1.758 | 1 |
| 60 | 52.85 | 1.732 | 1 |
| 61 | 55.02 | 1.669 | 1 |
| 62 | 55.70 | 1.650 | 2 |
| 63 | 56.45 | 1.630 | 3 |
| 64 | 57.45 | 1.604 | 5 |
| 65 | 58.81 | 1.570 | 1 |

*Intensity enhanced by ZSM-5.

EXAMPLE 2

In this example the same chemical formulation, i.e., the same silicate and the alum solutions, was used as in Example 1. The reaction mixture, obtained by mixing the silicate and the aluminate solutions, was held for 3 days at 300° F. in the reactor bomb, then for 7 days at ambient temperature, then for 3 more days at 300° F., for a total of 6 days at 300° F. The crystalline product was sampled and the sample was washed and dried according to the procedure of Example 1. X-ray diffraction analysis of the sample showed that the crystals had the x-ray diffraction pattern of the Table in Example 1. The zeolite was determined to be 100% ZSM-22.

EXAMPLE 3

In this example the same chemical formulation, i.e., the same silicate and the alum solutions, was used as in Example 1. The reaction mixture, obtained by mixing the silicate and the aluminate solutions, was aged for 3 days at ambient temperature prior to crystallization in the reactor bomb at 300° F. After 7 days of crystallization at 300° F. the sample was held for two days at ambient temperature, then crystallization was resumed at 300° F. for a total of 12 days at 300° F. The crystalline product was also analyzed by X-ray diffraction and it was determined to have the same pattern as shown in the Table of Example 1. The product was determined to the 105% ZSM-22.

In Examples 4–7, the ZSM-22 zeolite was prepared by an alternative method using hexanediamine as the organic compound. The full details of that method are disclosed in a commonly assigned U.S. patent application of E. W. Valyocsik, filed contemporaneously herewith, Ser. No. 06/629,743 now U.S. Pat. No. 4,902,406, the entire contents of which are incorporated herein by reference.

EXAMPLES 4–6

A solution of 28.6 parts colloidal silica (30 wt. % $SiO_2$) and 29.8 parts water was prepared. A solution of 1 part aluminum sulfate (17.2 wt. % $Al_2O_3$), 2.3 parts potassium hydroxide and 52.3 parts water was also made. These two solutions were combined and mixed for 15 minutes. Five parts of 1,6-hexanediamine were added to the solution and the entire mixture was stirred. This solution was put into a stirred autoclave and heated to 320° F. This temperature was maintained for 72 hours.

The resultant zeolite was then filtered and washed on a Buchner Funnel and then dried overnight at 250° F.

This preparation was prepared three consecutive times and the analyses are as follows:

| Example | 4 | 5 | 6 |
|---------|---|---|---|
| Zeolite | ZSM-22 | ZSM-22 | ZSM-22 |
| Crystallinity | 120% | 140% | 135% |
| $SiO_2/Al_2O_3$ Ratio | 64 | 61 | 64 |
| Na, wt. % | 0.13 | 0.10 | 0.13 |
| K, wt. % | 0.21 | 0.21 | 0.22 |
| N, ppm | 660 | 1170 | 670 |

The X-ray diffraction pattern of the as-synthesized zeolite of Example 5 is set forth below in Table II:

TABLE II

| Line | 2Theta | D(Å) | I/IMAX |
|------|--------|------|--------|
| 1 | 8.10 | 10.91 | 35 |
| 2 | 8.79 | 10.07 | 2* |
| 3 | 10.11 | 8.75 | 7 |
| 4 | 12.71 | 6.97 | 11 |
| 5 | 16.23 | 5.46 | 4 |
| 6 | 16.47 | 5.38 | 8 |
| 7 | 19.35 | 4.59 | 11 |
| 8 | 20.30 | 4.37 | 100 |
| 9 | 21.75 | 4.09 | 2 |
| 10 | 23.05 | 3.86 | 8* |
| 11 | 23.11 | 3.85 | 6* |
| 12 | 24.16 | 3.68 | 74 |
| 13 | 24.53 | 3.63 | 63 |
| 14 | 25.60 | 3.48 | 38 |
| 15 | 26.38 | 3.38 | 5 |
| 16 | 26.58 | 3.35 | 7 |
| 17 | 26.99 | 3.30 | 7 |
| 18 | 27.68 | 3.22 | 1 |
| 19 | 29.97 | 2.982 | 3 |
| 20 | 30.34 | 2.946 | 3 |
| 21 | 30.76 | 2.906 | 2 |
| 22 | 32.01 | 2.796 | 1 |
| 23 | 32.63 | 2.744 | 2 |
| 24 | 32.92 | 2.721 | 3 |
| 25 | 35.55 | 2.525 | 19 |
| 26 | 36.82 | 2.441 | 9 |
| 27 | 37.30 | 2.411 | 2 |
| 28 | 37.96 | 2.370 | 6 |
| 29 | 39.30 | 2.293 | 1 |
| 30 | 40.12 | 2.248 | 1 |
| 31 | 43.67 | 2.073 | 3 |
| 32 | 44.36 | 2.042 | 3 |
| 33 | 44.79 | 2.024 | 3 |
| 34 | 45.27 | 2.003 | 3 |
| 35 | 47.72 | 1.906 | 4 |
| 36 | 48.41 | 1.880 | 8 |
| 37 | 49.30 | 1.848 | 2 |
| 38 | 51.08 | 1.788 | 3 |
| 39 | 51.90 | 1.762 | 1 |
| 40 | 52.76 | 1.735 | 1 |
| 41 | 54.91 | 1.672 | 1 |
| 42 | 55.62 | 1.652 | 2 |
| 43 | 56.32 | 1.634 | 2 |
| 44 | 57.34 | 1.607 | 5 |
| 45 | 58.71 | 1.573 | 1 |

*Intensity enhanced by ZSM-5.

The data of Table II was obtained in the same manner as the data of Table I. Accordingly, the abbreviations and symbols of Table II have the same meaning as set forth above in connection with the discussion of Table I.

EXAMPLE 7

Catalyst Preparation from Zeolites of Examples 4–6

Samples of equal weight of zeolites of Examples 4–6 were combined and then mixed with alumina and water. This mixture was extruded into 1/16" pellets and dried.

The extruded material contained 65 parts ZSM-22 per 35 parts alumina.

The dried extrudate was calcined for three hours at 538° C. in flowing nitrogen. After cooling, the extrudate was twice contacted with an ammonium nitrate exchange solution (about 0.08 lb. NH₄NO₃/lb of extrudate) for one hour at room temperature.

The extrudate was then dried and calcined in air at 38° C. for six hours. The product analysis is as follows:

| | |
|---|---|
| Na, wt. % | 0.03 |
| N, ppm | 17 |

The alpha-test ($\alpha$-test) is an indication of the relative catalytic cracking activity of the catalyst compared to a standard catalyst. The value of $\alpha$ is the relative rate constant (rate of n-hexane conversion per unit volume of catalyst per unit time). It is based on the activity of fresh silica-alumina cracking catalyst taken as $\alpha=1$.

The $\alpha$-test is further described in a letter to the editor, entitles "Superactive Crystalline Alumino-Silicate Hydrocarbon Cracking Catalysts", by P. B. Weisz and J. N. Miale, Journal of Catalysis, Vol. 4, pp. 527-529 (August 1965) and in U.S. Pat. No. 3,354,078, the entire contents of both of which are incorporated herein by reference.

EXAMPLES 8-10

The catalyst of Example 7 was subjected to a feedstream of 50/50 by weight methanol and water at 30 psig pressure at 1 WHSV (methanol) to produce ethylene. The results and conditions of the three Examples are summarized below.

| | Example | | |
|---|---|---|---|
| | 8 | 9 | 10 |
| Temperature, °F. | 672 | 700 | 725 |
| Methanol Conversion, % by wt. | 47.5 | 60.2 | 68.8 |
| Ethylene Selectivity, % by wt. | 21.3 | 17.9 | 13.7 |

EXAMPLE 11

Heavy Stock Catalytic Dewaxing 17.6 grams of the catalyst of Example 7 was mixed with 88 grams of furfural raffinate in a pressure reactor. The reactants were allowed to react for 130 minutes at 500 psig. The results of the runs, for a product having boiling point (BP) of 650° F. or above, are summarized below.

| Run | Reaction Temp. °F. | Pour Point °F. | VI (Viscosity Index) |
|---|---|---|---|
| A | 600 | 90 | 99.9 |
| B | 550 | 65 | 106.8 |

The properties of the feedstock are set forth below. The objective of this example was the reduction of the amount of high molecular weight paraffins (waxes) so that the resultant hydrocarbon stock can be processed into more desirable products. As the above data indicates, the pour point of the feedstock was reduced considerably, indicating that ZSM-22 is an effective dewaxing zeolite.

| | |
|---|---|
| Gravity, API | 29.2 |
| Pour Point, °F. | 105 |
| KV @ 100° C., Centistokes | 9.260 |
| KV @ 130° C., Centistokes | 38.72 |
| Carbon Residue, wt. % (RCR*) | 0.11 |
| Sulfur, wt. % | 0.74 |
| Nitrogen, wt. % | 42. |
| Refractive Index @ 70° C. | 1.46513 |
| Aniline Point, °F. | 233 |

*Rems Carbon Residue

| Vacuum Distillation, % by Wt. | BP, °F. |
|---|---|
| — | 769 |
| 5 | 825 |
| 10 | 845 |
| 30 | 878 |
| 50 | 897 |
| 70 | 911 |
| 90 | 931 |
| 95 | 937 |

It will be apparent to those skilled in the art that the specific embodiments discussed above can be successfully repeated with ingredients equivalent to those generically or specifically set forth above and under variable process conditions.

From the foregoing specification one skilled in the art can readily ascertain the essential features of this invention and without departing from the spirit and scope thereof can adopt it to various diverse applications.

What is claimed is:

1. A process for converting lower alcohols and/or related oxygenates to gasoline-grade boiling hydrocarbons comprising contacting a feedstock of methanol and/or related oxygenates with a zeolite catalyst comprising ZSM-22 under such temperature and pressure conditions to convert at least a portion of the feedstock to gasoline-grade hydrocarbons.

2. A process of claim 1 wherein said contacting is conducted in the fluidized bed reactor at a temperature of at least 500° F., at pressure of 1 to 200 atmospheres and at 0.5 to 50 LHSV.

3. A process for converting lower alcohols and/or related oxygenates to gasoline-grade hydrocarbons comprising contacting a feedstock of methanol and/or related oxygenates with a gamma-alumina catalyst in a first reactor to convert at least a portion of the feedstock to dimethyl ether (DME) and subsequently contacting the effluent of the first reactor with a zeolite in a second reactor under such temperature and pressure conditions to convert at least a portion thereof to gasoline-grade hydrocarbons, wherein said zeolite is ZSM-22.

* * * * *